(12) United States Patent
Dagnello et al.

(10) Patent No.: US 10,799,654 B2
(45) Date of Patent: Oct. 13, 2020

(54) INTEGRATED DISTRIBUTED CLASSIFICATION, PREDICTION AND RESPONSE SYSTEM

(71) Applicant: CloudMode Corp., Winnetka, IL (US)

(72) Inventors: John Thomas Dagnello, Bexley, OH (US); John Thomas Wellehan, Winnetka, IL (US)

(73) Assignee: Cloudmode Corp., Winnetka, IL (US)

( * ) Notice: Subject to any disclaimer, the term of this patent is extended or adjusted under 35 U.S.C. 154(b) by 0 days.

(21) Appl. No.: 16/270,435

(22) Filed: Feb. 7, 2019

(65) Prior Publication Data

US 2019/0167927 A1    Jun. 6, 2019

Related U.S. Application Data

(63) Continuation of application No. PCT/US2017/063144, filed on Nov. 22, 2017.
(Continued)

(51) Int. Cl.
*A61M 15/00* (2006.01)
*A61M 11/00* (2006.01)
(Continued)

(52) U.S. Cl.
CPC ....... *A61M 15/0066* (2014.02); *A24F 47/008* (2013.01); *A61B 5/0004* (2013.01);
(Continued)

(58) Field of Classification Search
CPC .............. A61M 15/0066; A61M 15/06; A61M 2205/3303; A61M 2205/3324;
(Continued)

(56) References Cited

U.S. PATENT DOCUMENTS

| 2005/0115561 A1* | 6/2005 | Stahmann | ............ A61B 5/0031 128/200.24 |
| 2010/0081957 A1* | 4/2010 | Hyde | .................... A61M 15/02 600/532 |

(Continued)

FOREIGN PATENT DOCUMENTS

| WO | WO-2016001921 A2 * | 1/2016 | ............. A61K 9/007 |
| WO | WO-2016001926 A1 * | 1/2016 | ............. A61K 9/007 |

OTHER PUBLICATIONS

International Search Report for International Application No. PCT/US2017/063144, dated Feb. 13, 2018 (2 pages).
(Continued)

*Primary Examiner* — Tu A Vo

(57) ABSTRACT

A computer-implemented method of determining the efficacy of a substance that is vaporized and inhaled by a user includes receiving a cartridge within a housing of a vapor inhalation device. The cartridge stores a substance therein. The housing has an opening at a first end thereof. A characteristic of the substance in the cartridge is measured. At least a portion of the substance in the cartridge is vaporized to create a vapor. The vapor is in fluid communication with the opening of the housing. At least a portion of the vapor flows through the opening at the first end of the housing. A characteristic of the at least a portion of the vapor flowing through the opening is measured. Data is analyzed to generate an output. The data includes substance data associated with the measured characteristic of the substance and vapor data associated with the measured characteristic of the vapor.

26 Claims, 6 Drawing Sheets

Related U.S. Application Data

(60) Provisional application No. 62/426,176, filed on Nov. 23, 2016.

(51) Int. Cl.
*A24F 47/00* (2020.01)
*G06N 20/00* (2019.01)
*A61B 5/00* (2006.01)
*A61M 15/06* (2006.01)
*A61B 5/16* (2006.01)

(52) U.S. Cl.
CPC ............ *A61B 5/165* (2013.01); *A61M 15/06* (2013.01); *G06N 20/00* (2019.01); *A61M 2205/13* (2013.01); *A61M 2205/3303* (2013.01); *A61M 2205/3324* (2013.01); *A61M 2205/3331* (2013.01); *A61M 2205/3553* (2013.01); *A61M 2205/50* (2013.01); *A61M 2205/52* (2013.01); *A61M 2230/00* (2013.01)

(58) Field of Classification Search
CPC ...... A61M 2205/3331; A61M 15/0021; A61M 15/0023; A61M 15/0025; A61M 15/0026; A61M 15/008; A61M 2205/8206; A61M 2205/609; A61M 15/001; A61M 11/00; A61M 11/08; A61M 11/06; A61M 15/0001; A61M 15/0003; A61M 15/0065; H04W 4/029; G06N 20/00; A24F 47/008; A61B 5/0004; A61B 5/165; G05B 19/042; G06F 17/30587

See application file for complete search history.

(56) References Cited

U.S. PATENT DOCUMENTS

| | | | | |
|---|---|---|---|---|
| 2011/0225008 A1* | 9/2011 | Elkouh | ............... | G06F 21/6245 705/3 |
| 2012/0183949 A1* | 7/2012 | Hyde | ............... | A61B 5/082 435/5 |
| 2012/0247466 A1* | 10/2012 | Avni | ............... | A61M 15/0065 128/203.15 |
| 2014/0243749 A1* | 8/2014 | Edwards | ............... | A61M 5/31 604/187 |
| 2015/0245654 A1* | 9/2015 | Memari | ............... | A24F 15/12 141/2 |
| 2016/0029962 A1* | 2/2016 | Hyde | ............... | A61B 5/117 600/301 |
| 2016/0166785 A1* | 6/2016 | Morrison | ............... | A61M 11/00 128/200.14 |
| 2016/0166786 A1* | 6/2016 | Kinzer | ............... | A61M 11/041 128/200.14 |
| 2016/0330999 A1* | 11/2016 | Cameron | ............... | B01B 1/005 |
| 2016/0331023 A1* | 11/2016 | Cameron | ............... | A24F 47/002 |
| 2016/0331026 A1* | 11/2016 | Cameron | ............... | A24F 47/002 |
| 2016/0331027 A1* | 11/2016 | Cameron | ............... | A24F 47/002 |
| 2016/0331034 A1* | 11/2016 | Cameron | ............... | A24F 47/008 |
| 2016/0331036 A1* | 11/2016 | Cameron | ............... | H04M 1/7253 |
| 2016/0334119 A1 | 11/2016 | Cameron | | |
| 2016/0337362 A1* | 11/2016 | Cameron | ............... | H04L 63/10 |
| 2016/0337444 A1* | 11/2016 | Cameron | ............... | H04L 67/10 |
| 2016/0354562 A1* | 12/2016 | Morrison | ............... | A61M 15/0001 |
| 2016/0363570 A1* | 12/2016 | Blackley | ............... | G01N 33/0006 |
| 2017/0055588 A1* | 3/2017 | Cameron | ............... | H05B 3/44 |
| 2017/0106153 A1* | 4/2017 | Davidson | ............... | A61K 9/007 |
| 2017/0136193 A1* | 5/2017 | Cameron | ............... | A61M 11/042 |
| 2017/0136194 A1* | 5/2017 | Cameron | ............... | A61M 11/042 |
| 2017/0165439 A1* | 6/2017 | Kaufmann | ............... | A61M 15/0041 |
| 2017/0181223 A1* | 6/2017 | Sur | ............... | H04B 5/0081 |

OTHER PUBLICATIONS

Written Opinion of International Searching Authority for International Application No. PCT/US2017/063144, dated Feb. 13, 2018 (10 pages).

T. Hastie, et al.; "The Elements of Statistical Learning: Data Mining, Inference, and Prediction," Second Ed.; Springer; pp. 1-2, 9-11; Feb. 2009 (764 pages).

* cited by examiner

INTEGRATED DISTRIBUTED CLASSIFICATION, PREDICTION AND RESPONSE SYSTEM

CROSS-REFERENCE TO RELATED APPLICATIONS

This application is a continuation of International Application No. PCT/US2017/063144, filed on Nov. 22, 2017, which claims priority to and the benefit of U.S. Provisional Patent Application No. 62/426,176, filed Nov. 23, 2016, each of which is hereby incorporated by reference herein in its entirety.

FIELD OF PRESENT DISCLOSURE

The present disclosure relates generally to vapor inhalation systems and methods, and more particularly, to vapor inhalation devices and computerized methods for developing consumer specific models of efficacy for therapeutic and recreational use management based on dynamic modeling of consumer physiology, consumer experiential feedback, consumer use behavior, specific products, and environmental factors.

BACKGROUND

Accurate, real-time feedback on the efficacy and effect of consumption of chemical compounds and other substance characteristics inhaled or otherwise imparted into the human body is critical to developing meaningful insights and actionable recommendations to optimize efficacy, safety, consumption, and distribution of the substance carriers of these compounds. However, due to the myriad of factors that can also produce a change in a psycho-physiological affect in a human independent of consumption of chemical compounds, identifying to a high degree of confidence causality between consumption and particularly detected changes in affect or physiological state is a daunting endeavor. Erroneous causalities can be dangerous at worst, ineffective at best. On the other hand, pinpointing causalities can produce significant prodromal detection and amelioration following remedial action before the onset of dangerous or life-threatening conditions.

Vaping devices, including electronic vaping devices or e-vape devices, allow the delivery by inhalation of vapor containing one or more active ingredients. Electronic vaping devices are gaining increasing popularity both for prescriptive medical use and for consumption of cannabis and nicotine. Electronic vaping devices in particular may be portable, self-contained, and convenient for use. Unfortunately, the consumer or patient experience using such devices may vary dramatically due to such variables as the identity of the active ingredients, the amount of vapor and/or active ingredient provided, the specific consumer's individual unique inhalation topography, the consumer's behavior of usage (such as frequency, timing, amount, occasion of consumption), and the consumer's physiological, emotional and cognitive response to consumption.

To date, attempts to improve the overall efficacy of vaping products have been unsatisfactory. Systems that only attempt to address one or two variables in the complex, multi-variable inhalation process often will not lead to a significant improvement in the efficacy experienced by the consumer; for example, only attempting to determine the amount of vapor and/or an active ingredient in the vapor incorrectly assumes all of the material will be inhaled without taking into consideration the individual variability of the consumer's unique inhalation topography or the individual variability of the consumer's unique range of variables associated with their physiological, emotional, and cognitive response to the consumption.

Such a complex, multi-variable analysis requires generation and capture of large sets of structured data and unstructured data to form a basis for analysis and then recommendations and predictions for optimizing consumer behavior and product offering. The actual analysis methods of such structured and unstructured data are beyond current spreadsheet and basic modeling programs, thus requiring new machine learning methodologies to analyze and form recommendations and predictions for improved product and service offerings and improved consumer usage to optimize efficacy and experience. Machine learning is able to discover unanticipated dynamics of the product and service attributes, and consumer efficacy and experience related to the use of such service and product.

What is needed is a method and apparatus (e.g., system and/or device) for reliably and consistently optimizing the efficacy of the product by delivering vapor accurately (e.g., within a reasonable margin of accuracy/error, the delivered dosage and the identity of active ingredients) with an integrated consumer feedback mechanism based on actual usage (e.g., date, time, and frequency) and actual experienced effect (e.g. physiological, emotional and cognitive responses) to iteratively improve the efficacy regarding what is being consumed and how it is consumed.

For example, understanding which specific cannabis products might produce certain pharmacological effects if consumed in a certain form and dosage would be useful. Pharmacologically, cannabis is remarkably complex and barely understood. The cannabis plant contains at least 400 unique molecules whose actions and interactions remain largely unknown. In general, the currently marketed products that contain cannabis have widely varying pharmacological activity due to the fact that there are a multitude of nonuniformly-named strains of cannabis with widely varying concentrations of these chemicals. In addition, little is known on how the different available methods of consumption (smoking, vaping, edible, etc.) affect the individual. Further adding to the confusion, there is generally a lack of manufacturing control and quality control that ensures consistent and reproducible product. In general, current knowledge about cannabis expected dose and effect is minimal.

Furthermore, little is known about cannabis: the chemical compounds within it, the variance in cannabis offerings, the impact upon given cohorts of consumers, the impact of other behaviors, the preference dynamics, optimal formulations, and protocol for recreation and medical uses, and the optimal means for supporting business to provide goods, services and complementary offerings to the consumer.

SUMMARY

A multi-variable sensing system is disclosed. Sensors capture characteristics of the substance in a pre-vapor (e.g., liquid or solid) form, and when the substance is converted to vapor, at the moment of inhalation, and sensors capture attributes of the substance as the gaseous vapor depart from the vapor inhalation device and enter the user's lungs. Sensors close to or on the user's body capture one or more physiological characteristics of the user and/or other sensors capture one or more changes in a psycho-physiological affective state of the user. Optionally, self-reporting of subjective ratings, such as pain, pleasurableness, or mood, experienced by the user can be obtained. Optionally, external environmental factors can be captured by sensors, such as ambient temperature, light, noise, air quality, geolocation, and the like. Optionally, peer information can be captured, such as information about nearby or a community of inhalers in a social or crowd construct as a peer enhancer or to leverage peers to guide or bolster decision support.

The multi-variable sensing system can be realized as a real-time feedback system in which inhalation characteristics are captured while any combination of physiological or affective state responses, environmental characteristics, self-reported subjective ratings, and peer information are captured simultaneously to allow causality identification and outlier detection through one or more of machine learning, data mining, and statistical techniques. The feedback system includes a solid (or liquid) substance, which is transformed into a vapor, which is consumed by the human body, which in turn transforms the chemicals in the vapor to produce changes in physiology or affective state in the consuming body, and software that, among other things, causes adjustments to be made to the solid or liquid substance prior to a subsequent conversion into vapor form. Environmental characteristics and subjective self-reporting ratings can also be inputted to the software to further adjust the software's output. While the substance and vapor characteristics can be ascertained in a predictable, repeatable way, how a particular human body will react to different chemicals in the vapors is unknown and subject to many other influencers that are independent or very loosely correlated with the inhalation. Tangible, physical matter in the feedback system is transformed from solid/liquid to a gaseous phase by introduction of heat energy, and then diffused and transformed through a human body, producing changes in physiological and affective states. Sensors capture all of these input variables and feed them to a software system, which leverages machine learning, data mining, and/or statistical techniques to produce at least one output that is used to adjust the tangible matter until an optimum set of substance and vapor characteristics and corresponding changes to the affective and physiological states, optionally adjusted for independent environmental characteristics, is achieved.

According to some implementations of the present disclosure, an iterative feedback system includes a receptacle, a vaporizing element, a plurality of sensors, an interface, one or more memory devices, and logic circuitry. The receptacle is configured to receive therein a quantity of a tangible substance in liquid or solid form. The tangible substance has a set of substance characteristics. The vaporizing element is configured to convert at least a portion of the tangible substance into a corresponding vapor that flows into a smoke chamber before exiting an opening for inhalation by a human user. The receptacle and vaporizing element are parts of a vapor inhalation device. A first of the sensors is configured to detect a vapor characteristic of the vapor. A second of the sensors is configured to detect an environmental characteristic of an environment of the vapor inhalation device. The interface is configured to receive physiological data indicative of a physiological or affective state of a user of the vapor inhalation device in real-time as the first sensor is detecting the vapor characteristic. The one or more memory devices is configured to store outputs of the plurality of sensors and the physiological data together with associated timestamps. The logic circuitry is configured to receive the stored outputs and the physiological data and to generate an output that causes an adjustment to be made in the quantity of a tangible substance introduced into the receptacle, in at least one of the substance characteristics, or to a time duration or time period of usage of the vapor inhalation device.

According to some implementations of the present disclosure, a device includes a housing, a cartridge, a smoke chamber, a vaporizing element, a cartridge sensor, a vapor sensor, and an electronic memory device. The housing has an opening at a first end. The cartridge is positioned within the housing and stores a substance therein. The smoke chamber is within the housing and in fluid communication with the cartridge and the opening. The vaporizing element is positioned within the housing and adjacent to the cartridge such that the vaporizing element is configured to convert at least a portion of the substance in the cartridge into a vapor. The vapor is permitted to flow into the smoke chamber and out of the housing via the opening. The cartridge sensor is coupled to the housing and configured to measure a characteristic of the substance in the cartridge. The vapor sensor is coupled to the housing and configured to measure a characteristic of the vapor. The electronic memory device is configured to store data which include substance data associated with the measured characteristic of the substance and vapor data associated with the measured characteristic of the vapor.

According to some implementations of the present disclosure, a vapor inhalation and monitoring system includes a vapor inhalation device, an interface, and one or more processors. The vapor inhalation device includes a housing, a cartridge, a smoke chamber, a vaporizing element, and a vapor sensor. The housing has an opening at a first end. The cartridge is positioned within the housing and stores a substance therein. The smoke chamber is within the housing and in fluid communication with the cartridge and the opening. The vaporizing element is positioned within the housing and adjacent to the cartridge such that the vaporizing element is configured to convert at least a portion of the substance in the cartridge into a vapor. The vapor flows into the smoke chamber and out of the housing via the opening. The vapor sensor is coupled to the housing and configured to measure a characteristic of the vapor. The interface is configured to receive physiological data indicative of a physiological or affective state of a user of the vapor inhalation device. The one or more processors is configured to analyze the characteristics of the vapor and the physiological data to generate an output.

According to some implementations of the present disclosure, a vapor inhalation and monitoring system includes a vapor inhalation device, an interface, and one or more processors. The vapor inhalation device that has a housing, a cartridge, a smoke chamber, a vaporizing element, and a cartridge sensor. The housing has an opening at a first end. The cartridge is positioned within the housing and stores a substance therein. The smoke chamber is within the housing and in fluid communication with the cartridge and the opening. The vaporizing element is positioned within the housing and adjacent to the cartridge such that the vaporizing element is configured to convert at least a portion of the substance in the cartridge into a vapor. The vapor flows into the smoke chamber and out of the housing via the opening. The cartridge sensor is coupled to the housing and configured to measure a characteristic of the substance in the cartridge. The interface is configured to receive physiological data indicative of a physiological or affective state of a user of the vapor inhalation device. The one or more processors is configured to analyze the characteristics of the vapor and the physiological data to generate an output.

According to some implementations of the present disclosure, a computer-implemented method of determining the efficacy of a substance that is vaporized and inhaled by a user includes receiving a cartridge within a housing of a vapor inhalation device. The cartridge stores a substance therein. The housing has an opening at a first end thereof. A characteristic of the substance in the cartridge is measured. At least a portion of the substance in the cartridge is vaporized to create a vapor. The vapor is in fluid communication with the opening of the housing. At least a portion of the vapor flows through the opening at the first end of the housing. A characteristic of the at least a portion of the vapor flowing through the opening is measured. Data is analyzed to generate an output. The data includes substance data associated with the measured characteristic of the substance and vapor data associated with the measured characteristic of the vapor.

Additional aspects of the present disclosure will be apparent to those of ordinary skill in the art in view of the detailed description of various embodiments, which is made with reference to the drawings, a brief description of which is provided below.

BRIEF DESCRIPTION OF THE DRAWINGS

Features and advantages of the present disclosure will become more apparent from the following detailed description of exemplary embodiments thereof taken in conjunction with the accompanying drawings in which.

Figure 1:
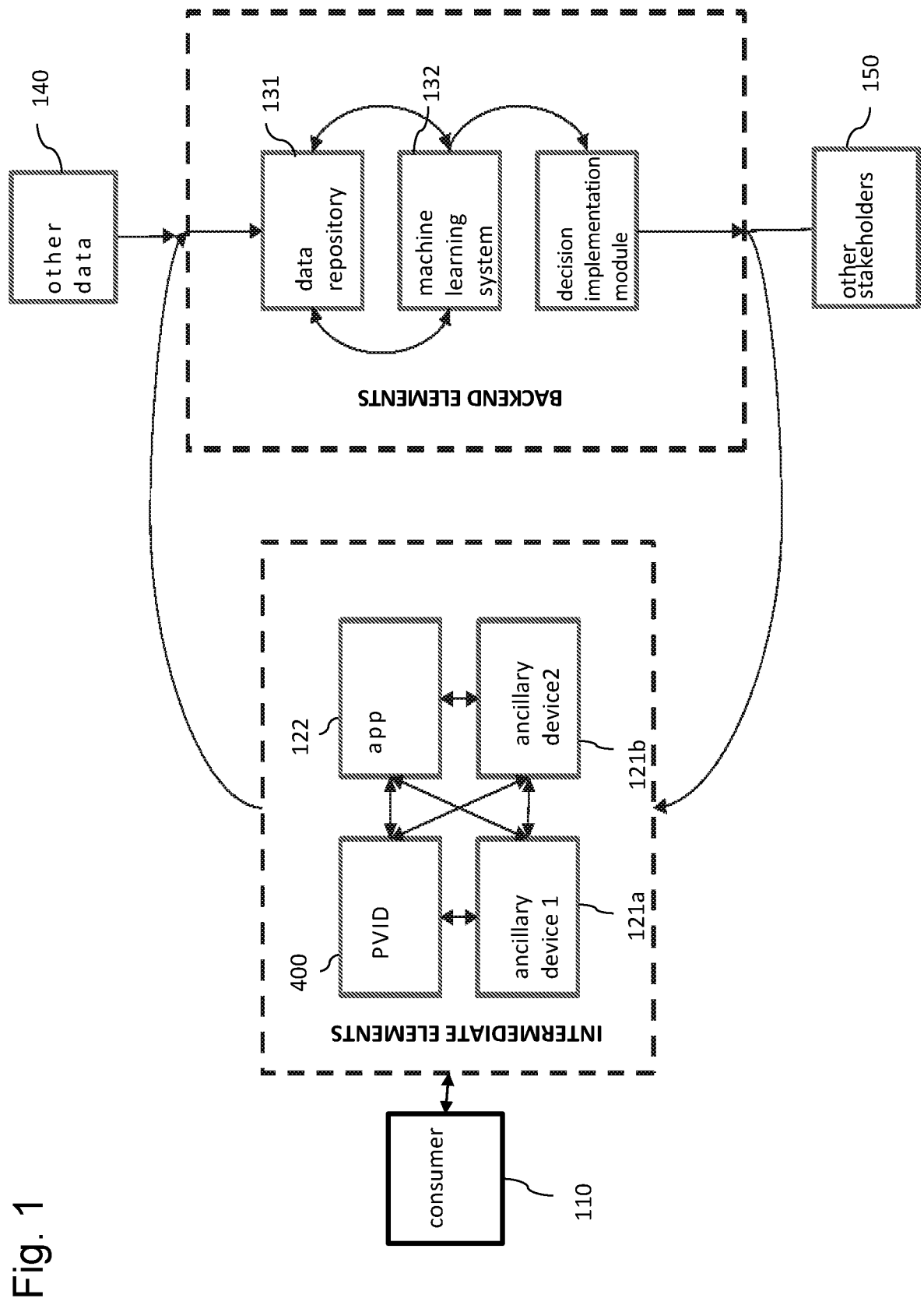
FIG. 1 illustrates a diagram for an exemplary method of dataflow within an embodiment of the system in general.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure is susceptible of embodiment in many different forms, there is shown in the drawings and will herein be described in detail preferred embodiments of the present disclosure with the understanding that the present disclosure is to be considered as an exemplification of the principles of the present disclosure and is not intended to limit the broad aspect of the present disclosure to the embodiments illustrated. For purposes of the present detailed description, the singular includes the plural and vice versa (unless specifically disclaimed); the word "or" shall be both conjunctive and disjunctive; the word "all" means "any and all"; the word "any" means "any and all"; and the word "including" means "including without limitation."

Several terms are defined below:

System: an integrated system and method of data generation, aggregation, and analysis, which is designed to describe and predict an outcome. The system is comprised of multiple networked components, communicating and coordinating their actions. These components may include a PVID, a data repository, a machine learning system, ancillary devices, and arrays of sensors.

PVID: personal vapor inhalation device ("PVID"); a device that transforms one or more substances into vapor, especially for inhalation.

Vapor: air containing diffused or suspended substance.

Substance: the vaporizable material often found within a cartridge; this may be liquid, viscous liquid, wax, loose leaf material or in another form.

Cartridge: a container holding a quantity of substance designed for insertion into a mechanism, such as, but not limited to a PVID.

Data repository: a computerized system collecting, organizing and storing both structured data and unstructured data.

Structured data: data with a high level of organization, such as, but are not limited to data generated by sensors or machines.

Unstructured data: data that is not organized in a predefined manner, resulting in irregularities and ambiguities, such as, but are not limited to, text, webpages, user forums, audio, and video.

Machine learning system: a computerized system that automates analytical model building, using algorithms that iteratively learn from data, enabling computers to find analytic insights without explicitly being programmed where to look. Methodologies include, but are not limited to deep learning and clustering.

Ancillary device: a device that provides additional complementary data, such as, but are not limited to, a mobile device, a computer, or a wearable device. An ancillary device may or may not host an app.

App: a program or piece of software designed to fulfill a particular purpose, such as, but not limited to, consumer interaction.

Consumer: a person who uses goods and services associated with the system.

Substance fingerprint: analytical evidence derived from data that uniquely characterizes a substance.

Label specification: a set or sets of data reflecting the attributes of a given substance as claimed by a brand or manufacturer. These attributes include, but are not limited to, ingredients and their concentration, strains, carriers, extraction methods and other processes, volume, chemical compounds, manufacturer, and manufacturing information (such as but not limited to, lot number, batch number, pallet number, traceability information, manufacturing plant, testing laboratory, product expiration date, brand claims, brand positioning, product descriptions, fonts, color, design and images, or any other quantitative or qualitative descriptors).

Strains: a group of like cannabis plants, which may reflect breed, stock, variety, genetics, consumer perception, or other attributes.

Sensor: a device that detects or measures a physical property, and records, indicates or otherwise responds to it.

Cartridge sensors: a group of one or more sensors in and around the PVID, the cartridge, and/or substance. These sensors collect information relating to cartridges and their contents.

Vapor sensors: a group of one or more sensors in and around the PVID that collects information relating to the generation of vapor, the physical nature of the vapor, the inhalation of the vapor, data associated with identification and attributes of the consumer inhaling the vapor, and the consumer's behavioral data.

Performance sensors: a group of one or more sensors in and around the PVID that collects information relating to the PVID's performance.

Physiological sensors: a group of one or more sensors in and around the PVID and ancillary devices that collect physiological data on a consumer. These sensors may record data during the period of usage of the PVID, during the period immediately surrounding usage, but also record data throughout periods of non-usage of the PVID.

Environmental sensors: a group of one or more sensors in and around the PVID, on ancillary devices, and other systems that allow for the collection of environmental data, such as, but not limited to ambient decibel level, amount of light, temperature, humidity, barometric pressure, elevation, location, movement. Amongst other things, the derived data can be used to understand consumer context, such as the aggregate circumstances that form the setting, for an event or activity.

Communication sensors: a group of one or more sensors that receive and/or transmit data.

BRAD profile: the baseline respiratory apparatus data ("BRAD") profile, which reflects the physical attributes of a consumer's respiratory apparatus (including but not limited to the mouth, pharynx, larynx, trachea, bronchi, lungs, diaphragm and other muscles) and structures that mediate the movement of air into and out of the body, as they activate through time. A BRAD profile incorporates physical attributes, such as, but are not limited to, the changing volume of air through time.

VID profile: the vapor inhalation data ("VID") profile, which reflects the physical nature of a consumer's individual inhalation of vapor from a PVID into the consumer's respiratory apparatus.

Vaping: the process of inhaling vapor from a PVID.

Vaporizing element: the component within a PVID that transforms a substance into vapor.

The consumer 110 inserts a cartridge 430 containing a substance 440 into their PVID 400. The PVID 400 uses an array of onboard cartridge sensors to collect data on one or more of the cartridge, substance, and label specification. The cartridge sensors quantify the attributes of the substance 440 along multiple dimensions, including, but not limited to, any one or more of direct and indirect measures of turbidity, color, chemical composition, viscosity, and flavor. For example, the system can be used with cannabis.

In one embodiment of the present disclosure, the substance turbidity is measured using one or more optical sensors emitting light and measuring refraction. In another embodiment of the present disclosure, the substance color is quantified using a spectrometer sensor, detecting absorption. In another embodiment of the present disclosure, the chemical composition of the substance 440 is measured using a nondispersive infrared sensor to identify specific compounds, such as, but not limited to, cannabinoids, terpenes, terpenoids, and flavonoids, by their resonance frequency. In another embodiment of the present disclosure, the substance capacitance is measured using capacitive sensors.

The one or more sensors can be activated by a number of triggers. In an embodiment of the present disclosure, the one or more sensors are triggered by a pressure-sensitive electrical or mechanical switch that is activated through the process of cartridge insertion. In another embodiment of the present disclosure, the sensors are triggered by an on/off switch 420 on the PVID 400. In another embodiment of the present disclosure, the sensors are triggered by an ancillary device 121 or a component of the system. In another embodiment of the present disclosure, the cartridge sensors are triggered by the activation of an onboard accelerometer within the PVID 400.

Upon activation, the cartridge sensors generate data describing the physical attributes of the substance 440 contained within the cartridge 430 along multiple dimensions, such as those described above. The data from each of these dimensions generates a distinctive pattern of data for a given substance 440, which the system subsequently analyzes, as described in the machine learning system section.

The system records cartridge and substance data generated by the cartridge sensors. The system records brand data and label specifications for the cartridge 430 and substance 440 through PVID 400, ancillary device 121, or apps. In one embodiment of the present disclosure, the PVID 400 uses a sensor tag, such as, but not limited to, an RFID chip embedded in the cartridge 430. In another embodiment of the present disclosure, the app 122 enables a drop-down menu for selection. In another embodiment of the present disclosure, the system captures package or sales transaction receipt information embedded in machine-readable optical label with sensors on an ancillary device 121 such as a camera or scanner, linking it to the label specifications. In another embodiment of the present disclosure, the system captures brand and product information by capturing an image of the packaging or cartridge 430 through an ancillary device 121; the communication sensors 464 then transmit the image data to the data repository 131; the machine learning system 132 then transforms and groups the data through pattern recognition algorithms; the initial image data is thereby transformed into brand data with label specifications for further analysis and stored and the data repository 131.

The cartridge sensors also, directly or indirectly, measure the volume of the substance 440 within the cartridge 430. In one embodiment of the present disclosure, an ultrasonic emitter generates a sonic chirp into the cartridge 430; the ultrasonic receiver captures the sonic response as the waves travel through the air bubble within the cartridge 430. As the substance 440 within the cartridge 430 decreases, the air within the cartridge 430 increases. The sensors record the changing nature sonic chirp as it passes the air bubble, thereby collecting data for subsequent processing by the machine learning system 132, ultimately determining the amount of remaining substance 440. In another embodiment of the present disclosure, we use a light sensor to measure the growing size of the air bubble. In another embodiment of the present disclosure, we use a light sensor to measure the substance 440 directly. In another embodiment of the present disclosure, we use an ultrasonic sensor to measure the substance 440 directly.

After recording the cartridge sensor data and storing the same in an electronic memory device, the system transmits the recorded data through the communications sensors to the data repository 131 where it can be stored.

Upon insertion of the cartridge 430 into the PVID 400, the consumer 110 may begin vaping. The consumer 110 activates the PVID 400, which turns on the vaporizing element 480 and vapor sensors 410*b*, through a number of potential triggers.

In one embodiment of the present disclosure, the vaporizing element 480 and vapor sensors 410*b* are triggered by a sensor on the PVID 400's mouthpiece 410*a*; the sensor can be, a PH sensor, an airflow sensor, pressure sensor, or other sensor. In another embodiment of the present disclosure, the vaporizing element 480 and vapor sensors 410b are triggered by an on/off switch 420 on the PVID 400. In another embodiment of the present disclosure, the sensors are triggered by an ancillary device 121 such as a smartphone, or another system. In another embodiment of the present disclosure, the vaporizing element 480 and vapor sensors 410b are triggered by the activation of an onboard accelerometer sensor within the PVID 400.

In addition, activation of the PVID 400 can trigger the activation of cartridge sensors, vapor sensors 410b, physiological sensors 463, environmental sensors 462, performance sensors 461, affectivity sensors, and/or communication sensors 464, the activation of which may in turn prompt data transfer and storage between system components.

In addition, a specific request generated by another component of the system can trigger the activation of cartridge sensors, vapor sensors 410b, physiological sensors 463, environmental sensors 462, performance sensors 461, affectivity sensors, and/or communication sensors 464, the activation of which may in turn prompt data transfer and storage between system components.

With the initial consumer 110 usage of the system, the consumer 110 generates baseline data, such as, but not limited to, inhalation data from the vaping sensors. The system generates and captures two types of descriptive inhalation data, both of which can be described as topographies.

The topographies are complex geometric shapes generated by sensor data that describe the changing rates of inhalation versus the units of time, and potentially other complementary factors. Analysis of large sets of complex, geometric forms, like topographies, is difficult and time-consuming with the current preferred state of analytical methodologies for respiration. Thus, the current standard respiratory measures, such as peak airflow and duration of inhalation, are designed to reduce data to single data points. This reduction simplifies the subsequent analysis of the data, but at the cost of information loss.

In contrast, the system uses a machine learning system 132 to analyze these complex, information-rich, topographies. The machine learning systems identify patterns (220), using methodologies (230) such as, but not limited to, clustering analysis and deep learning to describe, to predict, and to gain new insights. The result of such a process can generate an insight that prompts a specific recommendation, such as suggesting that a consumer 110 change posture while inhaling, for example. As another example, the machine learning system 132 may also predict impending issues for the consumer 110 such as early onset of COPD, and notify the consumer 110.

Figure 3:
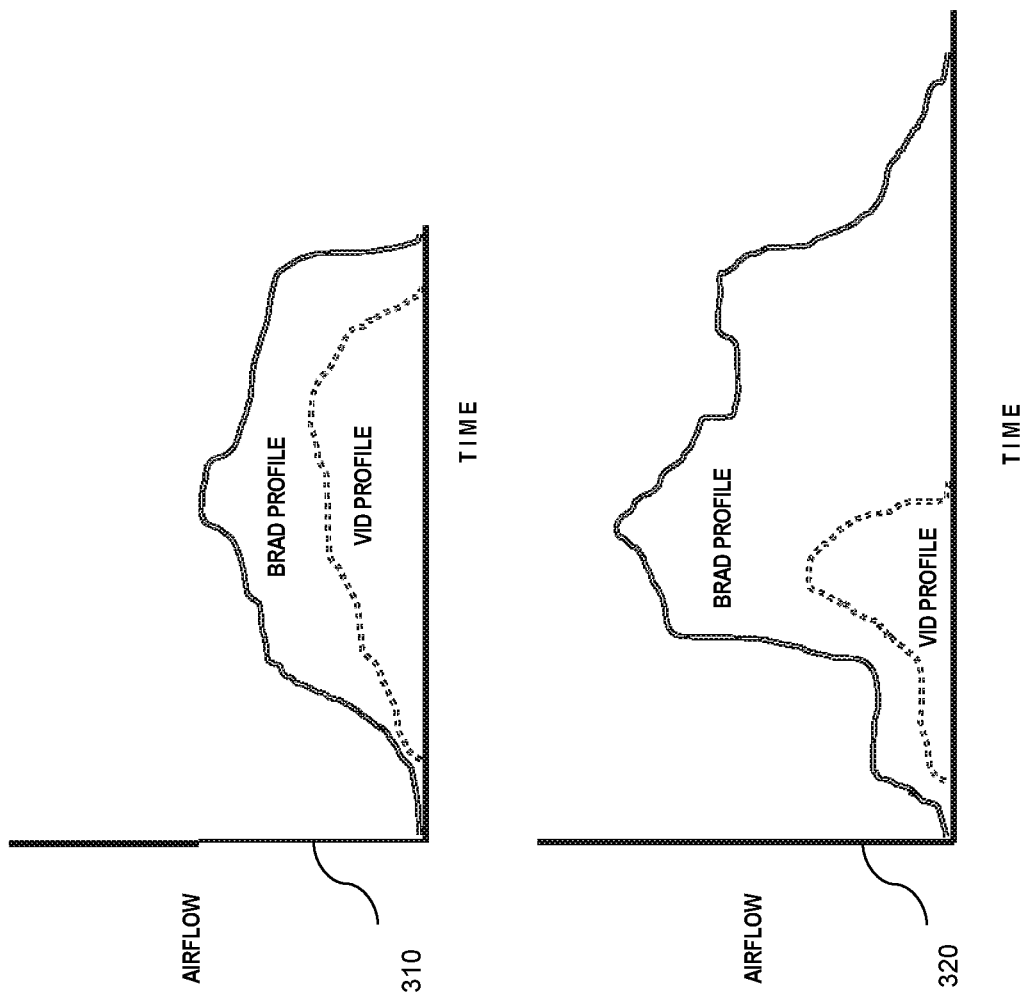
FIG. 3 illustrates exemplary BRAD profiles and VID profiles for two individuals.

The first type of descriptive inhalation data, baseline respiratory apparatus data profile (BRAD profile), reflects the physical attributes of a consumer's (e.g., consumer 110) respiratory apparatus, including but not limited to the mouth, pharynx, larynx, trachea, bronchi, lungs, diaphragm and other muscles and structures that mediate the movement of air into and out of the body. The second type, vapor inhalation data profile (VID profile), reflects the physical nature of an individual inhalation of vapor by the consumer 110 from the PVID 400 into the respiratory apparatus of the consumer 110. Two example charts 310, 320 showing a BRAD profile and the corresponding VID profile are shown in FIG. 3.

The system can generate the BRAD profile a variety of ways. In an embodiment of the present disclosure, the system can prompt the consumer 110 to generate a BRAD profile. In another embodiment of the present disclosure, an app 122 on ancillary device 121, such as but not limited to a mobile phone, prompts the consumer 110 with a visual or auditory message 530; the message directs the consumer 110 to generate a BRAD profile by respiring through a device, such as but not limited to the PVID 400. In another embodiment of the present disclosure, other flowmeters or drug delivery devices can be used to generate a BRAD profile. In an embodiment of the present disclosure, a vapor sensor, such as but not limited to, an airflow meter onboard the PVID 400, simultaneously collects data reflecting the inhaled volume of air and units of time. In an embodiment of the present disclosure, the system prompts the consumer 110 to exhale fully and then inhale fully through the PVID 400 mouthpiece until the respiratory apparatus of the consumer 110 held the maximum capacity of air. The consumer 110 then exhales, which can be recorded. The consumer 110 can optionally be asked to repeat this process multiple times. In addition, the system can prompt the consumer 110 for other complementary structured data and unstructured data.

The changes in the rates of flow as the respiratory cavity fills with air during inhalation, or empties during exhalation, reflect the dynamic functional constraints of the respiratory apparatus unique to a given consumer 110. For example, during the early stages in the inhalation process for a given consumer 110, the pharynx or vocal fold may systematically constrain the airflow. At a later stage of the same inhalation for the same consumer 110, the diaphragm may become the constraining element, for example. Thus, by capturing the idiosyncratic pattern of air movement and capacity, the system generates a BRAD profile.

In another embodiment of the present disclosure, the system generates a BRAD profile by taking measurements at many discrete points to approximate a continuous topology. In another embodiment of the present disclosure, the system can increase the dimensions of the BRAD profile by adding additional sensors. For example, a carbon dioxide, oxygen, or other sensor can measure the chemical composition of the inhalation or exhalation, and, along with the airflow and time, can generate a three-dimensional topography.

In addition to inhaling and exhaling at maximal capacity, the system can prompt the consumer 110 for and record other respiratory behaviors (532), such as a more moderate volume, or even relaxed breath in which the consumer 110 breathes normally through the PVID 400. These additional topographies add descriptive value to the BRAD profile, generating a more robust quantitative description of the performance of the respiratory apparatus of the consumer 110 under different conditions.

The second type of descriptive inhalation data, the VID profile, reflects the physical nature of an individual's actual, in-use inhalation of vapor by the consumer 110 from the PVID 400 into the respiratory apparatus of the consumer 110.

Each time the consumer 110 uses the PVID 400, the system generates a new VID profile idiosyncratic to that use event. The vapor sensors 410b record a continuous description of the inhalation of vapor 490 from the PVID 400 into the respiratory apparatus of the consumer 110. In an alternative embodiment of the present disclosure, the VID profile can be generated in multiple discrete points of measurement to approximate a continuous measure. As with the BRAD profile, additional dimensions can be added to the VID profile using additional sensors.

As described in the machine learning system discussion, the relationship between the BRAD profile and VID profile datasets provide the basis for additional analysis, rendering new insights. In the event where no BRAD profile or VID profile is available, data from other sources are extracted to statistically estimate what the missing inputs could be. For example, user profile information 653 (such as location, gender, height, weight, medical conditions) can be extracted from social media accounts 651, and/or mobile phone metadata. In one embodiment of the present disclosure, a user is asked to self-report user profile information 653 with its minimum requirement being set to gender and weight.

In addition to the BRAD profile and VID profile, the vapor sensors 410b generate data that directly or indirectly describes the nature of vapor. This data includes, but is not limited to, light refraction of vapor, light absorption of vapor, chemical compounds within vapor, vapor density, vapor temperature, vapor volume, vapor capacitance, and sonic vapor profile. The vapor sensors 410b also generate data that directly or indirectly describes the behavior of the consumer 110. This data includes, but is not limited to, accelerometer data, magnetometer data, gyroscopic data, mouth-piece PH data, airflow data, and time and location data.

The vapor sensor data collection is complemented with physiological sensor data and environmental sensor data. As described in the machine learning system discussion, the system generates novel descriptive and predictive insights by analyzing the union of data from the seemingly disparate data sets derived from one or more of any combination of cartridge sensors, vapor sensors 410b, physiological sensors 463, environmental sensors 462, and the app.

The physiological sensors 463 generate data that directly or indirectly describes the consumer's (e.g., the consumer 110) physiological functioning, affect and activity. The physiological sensors 463 generate data such as, but not limited to, heart rate data, galvanic skin response and electroconductivity data, and blood pressure data, accelerometer data, magnetometer data, gyroscopic data, location and time data, blood volume pulse and blood oxygen data.

In addition to measuring affective state through physiological sensors 463, like heart rate and galvanic skin response, other affective measures can be used. In some embodiments, the assembly could gather image and/or sound data for affective facial expression recognition, affective pupil dilation, and affective vocal pattern recognition, for example.

The environmental sensors 462 generate data that directly or indirectly describes the consumer 110's environment, occasions and events, such as, but not limited to, location and time data, ambient noise and light data, and temperature, barometric pressure and humidity data.

The performance sensors 461 generate data that directly or indirectly describes the performance of the PVID 400 and its components, such as, but not limited to, the battery data, the vaporizing element data, accelerometer data, and location and time data.

The application or the app 122 can gather information-rich data by prompting the consumer 110 for data or collecting it autonomously. In one embodiment of the present disclosure, the app 122 can prompt the consumer 110 to rate their experience or sense of wellness, before, during and after PVID usage, for example, rating it from a scale from one to ten or other suitable range, or using a variant of the wong-baker faces pain rating scale. In another embodiment of the present disclosure, the app 122 can request access to the user's social network accounts and/or mobile phone data. In another embodiment of the present disclosure, the app 122 can request qualitative preference data of the user, such as taste, smell, sensory perception data, or data reflecting enjoyment of a specific substance or brand, or data reflecting perceived PVID performance. This qualitative preference data can directly or indirectly describe aspects of PVID and substance usage. This qualitative preference data can also directly or indirectly describe the consumer 110. For example, this data can directly or indirectly reflect consumer activities, consumer response to other products and services, such as food preference, transportation preference, or other areas of interest. In another embodiment of the present disclosure, the app 122 can request health data that directly or indirectly reflects fitness, health conditions, and medications taken, and other information. In another embodiment of the present disclosure, the app 122 can request ancillary device data, network data, proximate network device data, or social media data.

The consumer can interact with the system through the app, or other components. For example, the consumer 110 can adjust or set the PVID vaporization settings through an app's graphical user interface, natural language processing, or by other means. In an embodiment of the present disclosure, the consumer 110 can adjust the PVID 400 to either a cloud mode or discrete mode through the app, or other components. In another embodiment of the present disclosure, the consumer 110 can adjust the PVID 400 to emit flavored, scented, or colored vapor through the app, or other components. In an embodiment of the present disclosure, the consumer 110 can share data on social media or with healthcare providers through the app, or other components. In an embodiment of the present disclosure, the consumer 110 can earn rewards through behavior through the app, or other components. In an embodiment of the present disclosure, the consumer 110 can receive and respond to healthcare, or other, notifications through the app, or other components. In an embodiment of the present disclosure, the consumer 110 can use the app, or other components, to transact through the system, using currency, crypto-currency, like bitcoin, or other media of exchange.

The data repository 131 collects, organizes and stores both structured data and unstructured data. In one embodiment of the present disclosure, the data repository 131 resides on a computer server or multiple computer servers. In another embodiment of the present disclosure, the data repository 131 resides on the cloud. In another embodiment of the present disclosure, the data repository 131 is distributed across the system.

The data repository 131 includes data that can directly or indirectly describe consumers, or any other cohort, in a number of ways, such as, but not limited to physical description, social description, health description, dietary description, behavioral description, and cannabis usage description. Subsequent clustering analysis and cohort generation can be conducted along a number of dimensions by the machine learning system 132.

For example, physical description data may directly or indirectly reflect factors including, but not limited to weight, height, BMI, sex, age, heart rate, blood pressure, body temperature, blood oxygen, perspiration, electroconductivity of skin, EEG, ECG, glucose levels, body fat percentage, genomic, metabolomic, proteomic information, and other factors.

Social description data can directly or indirectly reflect factors including, but not limited to ethnicity, education, marital status, relationship status and stability, employment, occupation, social and familial connections such as children, siblings, parents, grandparents, and pets; death, separation, job loss and caregiving; financial status factors such as, income, homeownership, insurance status, FICO score, assets, demography related to location, zip code, commute, religious affiliation, legal history, including divorce, incarceration, bankruptcy, and moving violations, and other factors.

Health description data can directly or indirectly reflect factors including, but not limited to current and historical measures of disease, accidents, substance abuse, use of supplements, caffeine, legal and illicit drugs, alcohol and tobacco; healthcare coverage, stress level factors such as hours worked, days worked, vacation frequency, and management responsibility; sedentary behavior factors such as continuous hours of relative inactivity, locus of inactivity, frequency of inactivity; active behavior factors such as continuous hours of relative activity or exercise, locus of activity, frequency of activity.

Dietary description data can directly or indirectly reflect factors including, but not limited to restriction relating to preference, food intolerance, religious observance; locus of food consumption, timing, frequency, regularity, and quantity of consumption; food quality such as calories, protein, nutritional attributes, freshness, and degree of processing, and other factors.

Behavioral description data can directly or indirectly reflect factors including, but not limited to sleep attributes such as regularity, length, REM, sleeping environment such as temperature, ambient light and noise, sleeping partner; activity data, such as alcohol and caffeine consumption, exercise regularity, intensity, variance, and level of competition; entertainment such as internet use, level of social media engagement, including network size, degree of privacy, amount shared and amount observed; television viewing, reading, hobbies and shopping behavior; sexual activity, such as partner and frequency, and other factors; work activity, such as hours worked and intensity of work.

Cannabis usage data may directly or indirectly reflect factors including, but not limited to raw sensor data related to BRAD profile, VID profile, substance, strain, brand, frequency of use, time of day, amount consumed, reported benefit, locus of usage, PVID mode usage, purpose of use, sharing, PVID performance, physiological response, and cartridge depletion, and other factors.

Figure 2:
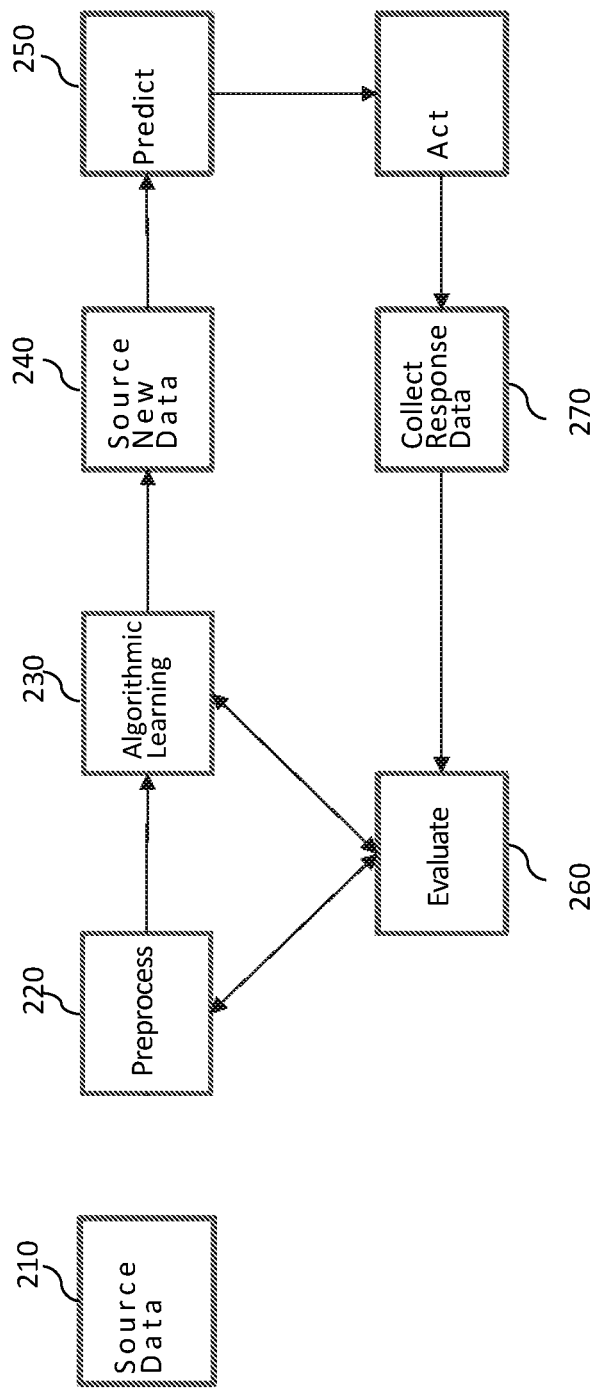
FIG. 2 illustrates a diagram for an exemplary method of workflow within an embodiment of the machine learning system.

The machine learning system 132 processes both structured and unstructured data from the data repository 131. For a given analysis, the machine learning system 132 extracts two distinct sets of data from the data repository 131: training data 210 and test data 240. The machine learning system 132 separates the data through which it develops its initial insights (training data 210) from the data set it uses to validate those insights (test data 240). The methodology used for separating the training data 210 from the test data 240 varies depending upon application. For example, when developing a predictive insight from a time series, like historical commodity pricing dynamics, like substance pricing, machine learning system 132s may develop descriptive and predictive models based on data up to a historical point in time, for example, for a duration from six years from present to one year from present (260); the most recent year can be used for test data 240 to validate and score the modeled prediction (250), as well as parameterize the model without overfitting it. Thereafter the machine learning system 132 may iterate, refining the modeled prediction or establishing a new hypothesis (230), such as shown in FIG. 2. In other applications, the machine learning system 132 can randomly separate the training data 210 from the test data 240 without respect to time. Likewise, the particular type of algorithm utilized by the machine learning system 132 can vary by application.

Much of the power of the machine learning system 132 is derived from its ability to identify patterns, and then group like raw and/or transformed data and metadata sets from any source or sources into cohorts for subsequent analysis. The machine learning system 132 typically transforms raw data into a data representation framing the information-rich feature variables; this is often done through feature selection or feature extraction. Thereafter, the machine learning system 132 classifies the data, enabling further analysis, leading to description and prediction of underlying dynamics reflected in the data.

For example, the machine learning system 132 can readily classify consumer cohorts, substance cohorts, BRAD profile cohorts, and other cohorts, enabling subsequent analysis and discovery. In addition to providing simple descriptive and predictive results, the machine learning system 132 also provides discovery through supervised, reinforced, and unsupervised learning. These insights can be made useful through information transfer and other actions.

In addition, effective cannabis consumption data can be derived by modeling the nonlinear relationship between BRAD profile, VID profile, and physiological response. The physiological and cannabis usage data can be transformed to descriptive and predictive models of the physiological response and self-reported efficacy data dynamics for an individual consumer 110 and consumer cohort. As another example, the BRAD profile, VID profile, and physiological response data 270 can be transformed by the machine learning system 132 through cluster analysis, and analyzed, generating descriptive and predictive models of both generate gross cannabis consumption data (the total cannabis consumed) and the effective cannabis consumption (the modeled amount of cannabis that is absorbed into the consumer 110's body) associated with inhalation.

Cannabis usage data can be transformed to generate descriptive and predictive measures of the magnitude of physiological change relative to effective consumption for an individual consumer and consumer cohort; magnitude of physiological response to substance fingerprint for an individual consumer and consumer cohort; correlation dynamics between brand preference and substance fingerprint preference for an individual consumer and consumer cohort; individual consumer and consumer cohort brand preference; individual consumer and consumer cohort substance fingerprint preference; individual consumer and consumer cohort purchase patterns; context of usage for an individual consumer and consumer cohort; time of substance depletion; preference and optimal substance choice for an individual consumer and consumer cohort with constrained options; complementary products or services for an individual consumer and consumer cohort; cannabis occasion classification and identification model for an individual consumer and consumer cohort; identification of the optimal substance for an individual consumer and consumer cohort; identification of the optimal usage protocol for an individual consumer and consumer cohort.

As described previously, the system records cartridge and substance data generated by the cartridge sensors, transmits it through the communications sensors to the data repository 131 where it is stored. The system records brand data and label specifications for the cartridge 430 and substance through PVID 400, ancillary device 121, or apps 122. In one embodiment of the present disclosure, the PVID 400 uses an RFID chip embedded in the cartridge 430. In another embodiment of the present disclosure, the app 122 enables a drop-down menu for selection. In another embodiment of the present disclosure, the system captures package or sales transaction receipt information embedded in machine-readable optical label with sensors on an ancillary device 121 such as a camera or scanner. In another embodiment of the present disclosure, the system captures brand and product information by capturing an image of the packaging or cartridge 430 through an ancillary device 121; the communication sensors 464 then transmit the image data to the data repository 131; the machine learning system 132 then transforms and groups the data through pattern recognition algorithms; the initial image data is thereby transformed into brand data with label specifications for further analysis and store and the data repository 131.

The substance data has multiple dimensions, including, but not limited to measures of turbidity, color, chemical composition, capacitance and viscosity, each of which may be distinctive for a given substance. In one embodiment of the present disclosure, the machine learning system 132 develops a series of substance fingerprints by first generating combinations of dimensions. A mathematical analysis illustrates that the potential number of substance fingerprints can become quite large, and intractable for a human analysis independent of machines; for example, the eleventh member of a factorial sequence produces 39,916,800 permutations. In one embodiment of the present disclosure, the machine learning system 132 correlates the substance fingerprints with brand and label specifications; in a related embodiment of the present disclosure, the system uses the correlated substance fingerprints and brand and label specifications to automatically identify the brand and label specifications from substance data generated by the cartridge sensors from a cartridge 430 inserted in a PVID.

The machine learning system 132 can employ classification and cluster analysis to identify like substance fingerprint into substance fingerprint cohorts, which can be used, amongst other things for subsequent analysis, such as substance usage, substance efficacy, substance preference, substance trend analysis, and substance formulation by consumer cohorts. In another embodiment of the present disclosure, similar analyses can be conducted by brand and label specifications.

For example, the system can be used to verify the identity of a substance within the cartridge 430, and that the substance, cartridge, label specifications and brand are internally consistent probabilistically from a data perspective. The system can notify the consumer, manufacturer or distributor of a probabilistic inconsistency, as well as flag related data points in the repository for potential data quality analysis. In one example scenario, the consumer can be prompted to reinsert the cartridge 430 to collect data of any type for reanalysis. In another scenario, the consumer can be prompted to remove the cartridge 430 for disposal, replacement or recall. The consumer derives utility by avoiding the accidental inhalation an unintended product, which can be counterfeit, expired, defective or mislabeled. Counterfeit, expired, and defective products may pose a health risk to the consumer. In a parallel manner, the manufacturer or distributor derives utility by identifying counterfeit or defective products in real time, enabling them to take action, such as a targeted recall. This minimizes the business and reputational risks.

Generalizing the example above, the machine learning system 132 can also model the data quality within the data repository 131, minimizing the impact of spurious data. In a similar manner, the machine learning system 132 can also model the quality of data generated by the performance sensors 461 and other sensors, the PVID 400 or another system component. In addition to minimizing the impact of spurious data, it enables the system to take a remediating action, such as, but not limited to, prompting the replacement of PVID 400, reactively or in advance of problem.

As another example, in addition to generating substance fingerprints for identification, the machine learning system 132 can detect deviations or changes in the substance fingerprints, which may indicate, amongst other things, substance decay, substance defect, and variance in substance data indicative of quality control issues. These observations by the machine learning system 132 can be made actionable by using communication sensors 464 to transmit notification of the identified deviations or changes. For example, this process would initiate a substance or cartridge recall process. As another example, this process would notify the consumer 110 to change the substance or cartridge 430. Further, this process can prompt or initiate an automatic cartridge order through our system, or cartridge replacement by the manufacturer or distributor (521). In a related example, the machine learning system 132 can transform the cartridge sensor data to describe or predict substance depletion within a cartridge, and prompt or initiate an automatic cartridge order through the system. In another example, this process would notify the manufacturer or distributor of quality control problems associated with the substance or cartridge 430. In another embodiment of the present disclosure, this process would generate insight into shelf life or product expiration date of a substance or cartridge 430, which can be shared with the consumer, improving their substance usage experience and satisfaction, thereby potentially increasing customer retention, as customer retention tends to correlate with satisfaction. In another example, this process would generate insight into shelf life or product expiration date of a substance or cartridge, which can be shared with the manufacturer and distributor 150, to optimize operations, processes and decision, such as, but not limited to, inventory management and production methods (522). As another example, the system can report real-time and historical data on substance, substance fingerprint, cartridge, label specification, or any cohort, by any other cohort, such as consumer. The manufacturers and distributors would derive utility by better understanding the consumer and their consumption. For example, manufacturers can adjust their formulation, their marketing, and their inventory according to the system's modeled results (522). Businesses, such as, but not limited to manufacturers and distributors, can derive additional utility through the system, through geolocation analysis of consumption. This would allow businesses to locate operations and assets proximate to the consumer, thus minimizing transportation times and costs. The modeled description and predictions derived from the machine learning system 132 enables the system to make bespoke recommendation to the consumer along any dimension. For example, the system can make bespoke recommendations by efficacy, preference or any other modeled factor or constraint, for example, inventory limitation.

In one embodiment of the present disclosure, the data repository 131 may also contain non-cartridge substance data, derived through label specifications, on a website, packaging, or other source; the machine learning system 132 can then classify the non-cartridge substances, such as edibles, in relation to like substance contained within cartridges; this classification process would provide the basis for preference and efficacy modeling for consumers, manufacturers and distributors of non-cartridge substances. For example, the system can recommend a particular edible, such as a substance infused chocolate, with data attributes like the model-derived preferred substance within a cartridge (531). Further, the system can generate descriptive and predictive models of and for the consumer from any number of data sets, or combinations thereof, pulled into the data repository 131. For example, the data repository 131 can acquire social media data, which the machine learning system 132 can then use together with other data sets 140, or isolation, to describe or predict consumer related behaviors, preference, actions, and change.

In an embodiment of the present disclosure, the system can be used for diagnosing, curing, mitigating, treating, or preventing disease. In an embodiment of the present disclosure, the system can be used for detecting, describing, or predicting prodrome or an early symptom or group of symptoms which indicate the start of an illness before other specific symptoms occur. In such an embodiment of the present disclosure, the present disclosure can be used for detecting, describing, or predicting specific symptoms which may occur in the prodrome of a specific illness. For example, the system can be used for detecting, describing, or predicting the precursor to the onset of a chronic neurological disorder such as migraine or epilepsy where prodrome symptoms can include but are not limited to aphasia, scotoma, euphoria, or photosensitivity. In further describing such an example, the system, such as, but not limited to, physiological sensor, environmental sensor, and consumer-generated app data can be transformed, through the machine learning system 132 to generate descriptive and predictive measures of the existence and magnitude of physiological or environmental change relative to the onset of symptoms and the course of a disease state. In such an example as applied to seizure disorders, and whereas prior art systems and algorithms determine that a seizure is occurring after detection of its actual onset, the system is directed to a method and apparatus for predicting that a seizure is going to occur sometime well in advance of any detectable clinical onset of seizure activity by monitoring data, extracting features from the data and deriving a fingerprint representing a combination of those features that are determined, through the machine learning system analysis of a particular individual and/or other knowledge of seizure prediction across a number of individuals, to be predictive of seizure onset, and analyzing the fingerprint with a trainable algorithm to predict seizure onset. Such a method can function on both an instantaneous basis and a historical basis as well as in different time frames, such as over days, hours, minutes, and seconds. Additionally, the system can interface with the consumer or healthcare professional by way of an ancillary device 121 or app 122 or other communication method that includes, but is not limited to, a display, an audible or visible alert, and a user interface, such that, the system can send a signal(s) indicating a probability of seizure occurrence within one or more specified periods of time. The consumer or healthcare professional may interact with the system via the ancillary device 121 or app 122 or other communication method to generate certain levels of alerts based on programmable probability thresholds or other methods. In an embodiment of the present disclosure, the system can be programmed to automatically trigger preventative actions, such as the delivery of one or more drugs, or the activation of a consumer behavior algorithm which can be employed to avoid the seizure or modulate the severity of a seizure (521). Outputs from the system can be used to train the patient in a biofeedback scheme to learn to avoid or mitigate the seizures themselves. In an embodiment of the present disclosure, the system can detect the probable onset of a grand mal seizure, and prompt the consumer to vape substance which mitigates or prevents the clinical manifestations (533). In a similar embodiment of the present disclosure, the system can be used for detecting, describing, or predicting non-specific symptoms, such as, but not limited to, lack of appetite, fever, headache or malaise which may occur in the prodrome of many infections or other illnesses.

In a similar embodiment of the present disclosure, the system can be used for developing and implementing disease treatment, disease mitigation, disease diagnosis, or disease prevention protocols, or specific consumer behavior algorithm(s).

In another embodiment of the present disclosure, the system can discover novel pharmacologically active ingredients or novel combinations of pharmacologically active ingredients or novel uses of pharmacologically active ingredients found in the substance or vapor. In another embodiment of the present disclosure, the system can identify the actual active ingredients which can differ from the reported active ingredient in the label specification. For example, the label specification may report THCA and CBD as the active ingredients, whereas the system identifies unreported compounds, such as, but not limited to, THCV, specific terpenes, or other compounds, as generating a profound effect.

Impairment

In an embodiment of the present disclosure, the system can be used to detect impairment, or directly or indirectly derived deviations from modeled baseline behavior. Such deviations can include, but are not limited to a temporary motor coordination abnormality, neurologic or other physiological abnormality. The system can describe and/or predict the state of the subject, including the presence of conditions or the ongoing development of conditions, such as, but not limited to, fatigue or intoxication.

As an example, the present disclosure is directed to a method and apparatus for predicting that motor or neurological impairment is developing or occurring by monitoring data, extracting features from the data and deriving a fingerprint representing a combination of those features that are determined, through the machine learning system analysis of a particular individual and/or other knowledge of impairment prediction across a number of individuals, to be predictive of impairment, and analyzing the fingerprint with a trainable algorithm to predict impairment onset or state. Such a method can function on both a real-time basis and a historical basis as well as along different time frames, such as over days, hours, minutes, and seconds. Additionally, the system can interface with the consumer by way of an ancillary device 121 or app 122 or another medium, including, but not limited to, a display, an audible or visible alert, and a user interface, such that, the system can send a signal(s) indicating a probability of or state of impairment occurrence within one or more specified periods of time. The consumer can interact with the system via the ancillary device 121 or app 122 or another communication method to generate certain levels of alerts based on programmable probability or occurrence thresholds, whether developed from the machine learning system 132 or other related systems. In addition, the system can be programmed to automatically trigger preventative actions, such as the inactivation of the PVID of a consumer for a period of time which can be employed to avoid the impairment or modulate the severity of impairment, or trigger other automatic actions, such as the delivery of alternative transportation for the consumer or a personal auto lock-out feature while impaired. Outputs from the system can be used to train the patient in a biofeedback scheme to learn to avoid or mitigate the impairment themselves. In a similar embodiment of the present disclosure, the present disclosure can be used for detecting, describing, or predicting other states of impaired motor coordination, such as, but not limited to, fatigue.

Figure 4:
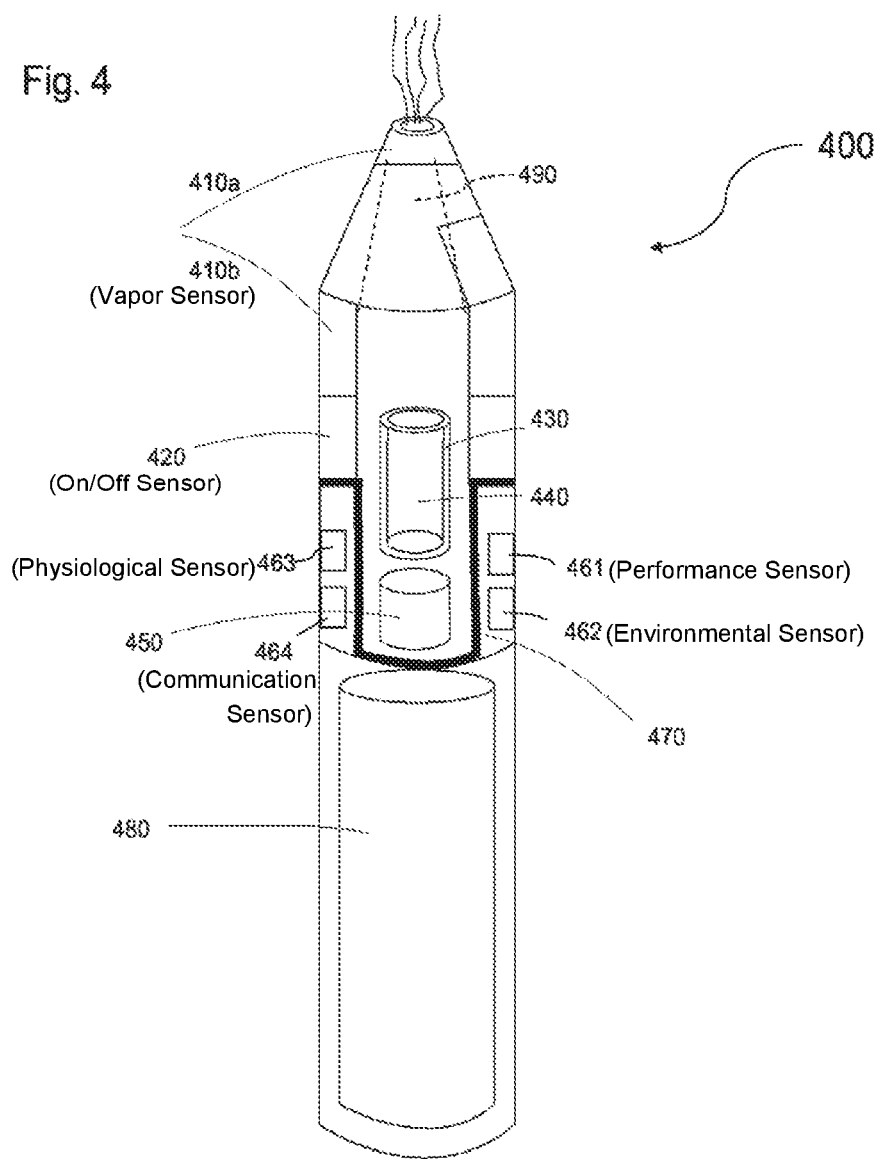
FIG. 4 illustrates exemplary aspects of an embodiment of a PVID.
Figure 5:
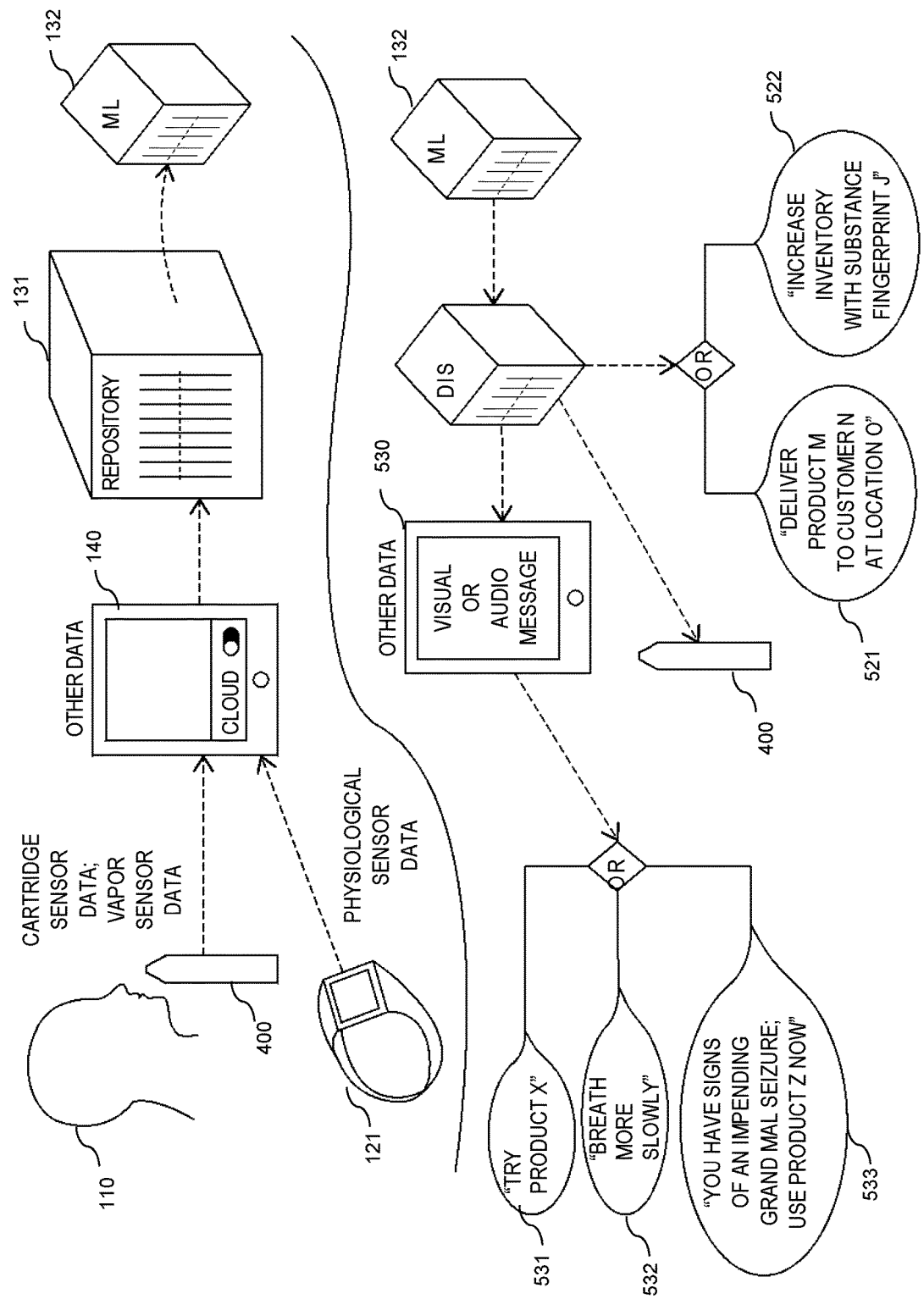
FIG. 5 illustrates a diagram for an exemplary method of system use.
Figure 6:
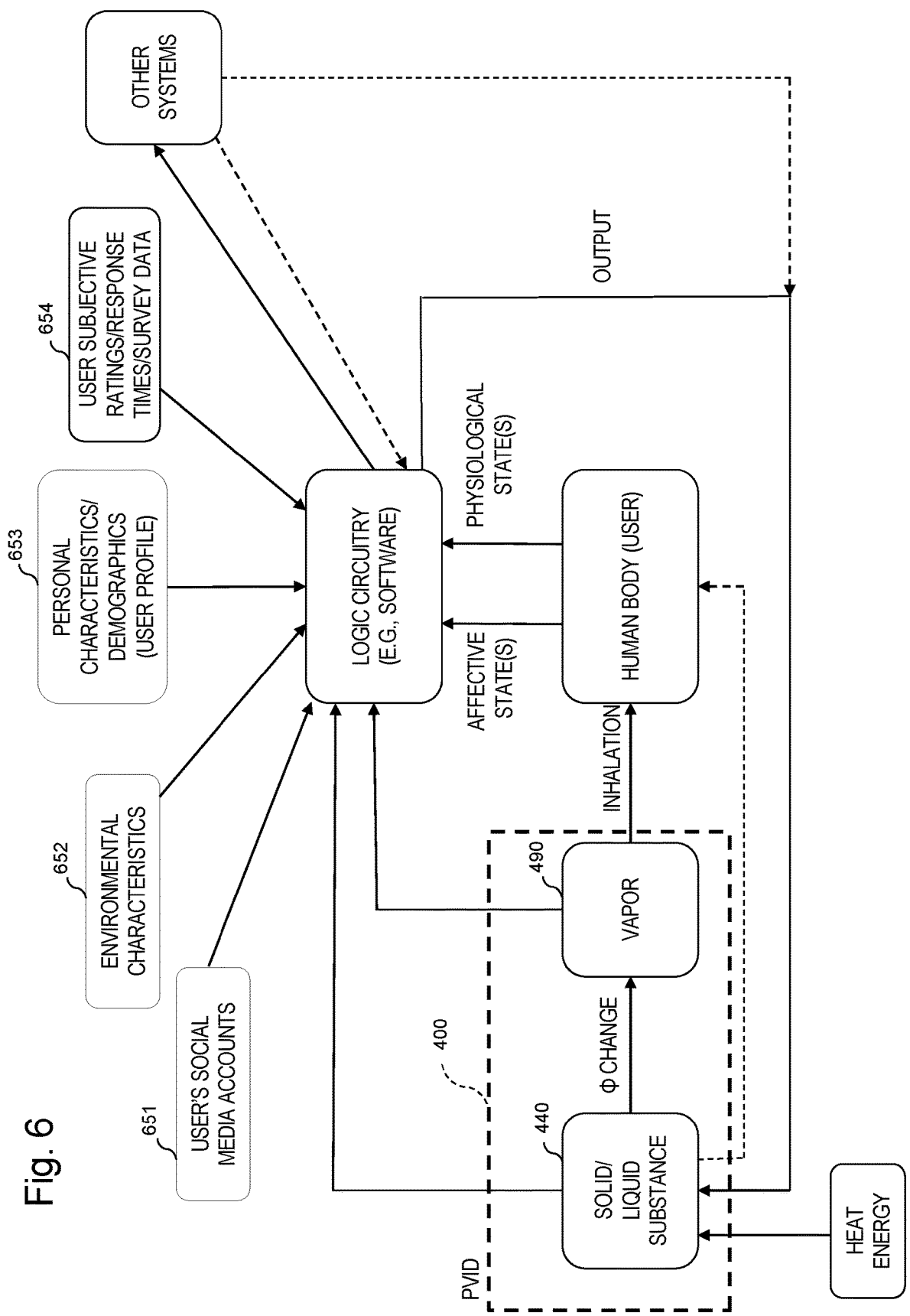
FIG. 6 illustrates a diagram for an embodiment of the iterative feedback system.

The system can also incorporate a PVID 400 with several unique improvements, such as shown in FIG. 4. In an embodiment of the present disclosure, the PVID 400 can house a cartridge warmer 450 that can adjust the substance viscosity to a desired level dynamically depending upon factors such as substance fingerprint, ambient temperature, or other factors. This decreases the functional variance of the PVID 400. In another embodiment of the present disclosure, the PVID 400 includes a thermal blanket 470 that insulates the sensors and other electronics from the vaporizing element 480. This increase the performance and useful life of a PVID 400. In an embodiment of the present disclosure, the PVID 400 houses an electronic controller that allows for dynamic adjustment of the vaporizing element 480 and other PVID components, enabling the system to significantly increase or decrease the amount and intensity of the vapor; this enables a consumer to minimize the amount of visible vapor for discrete use, or conversely, maximize the functional intensity as well as visible vapor cloud; the consumer can then dynamically adjust between a discrete mode and a cloud mode by interacting with the system, for example through the GUI, such as shown in FIG. 5. In another embodiment of the present disclosure, in addition to these two modes, the consumer can select a level of vapor intensity along the gradient between the two modes.

The system generates and collects objective data 652 describing elements of the physical world, such as, but not limited to, light refraction measurements of a substance and electroconductivity of skin. These data sets and unions of data sets can then be used as the basis for machine-generated systematic classification. The system also collects data along culturally induced subjective classifications, commonly perceived as object, such as, but not limited to, the concept of strain and the reported active ingredients. The system also collects data along subjective measures 654, such as reported product preference which may be influenced by confounding factors, such as brand biases and environment. The system can use the data to tease apart objective physical realities from the impact of cultural and perceptual biases. The system uses machine learning system 132 to generate novel insights reflected in these differences. The system uses these modeled insights for discovery, to provide decision support and to act.

Although many of the examples described herein are directed to determining usage and dosage of cannabis, it should be understood that these methods and apparatuses may be used for usage and dosage determination of any vaporizable material, including therapeutic drugs. Examples of active ingredients that may be used as described herein may include nicotine, botanicals, nutraceuticals, pharmaceuticals, and the like, including combinations of those.

While this disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the disclosure.

In the claims, any reference signs placed between parentheses shall not be constructed as limiting the claim. The word "comprising" does not exclude the presence of elements or steps other than those listed in a claim. The word "a" or "an" preceding an element does not exclude the presence of a plurality of such elements.

The mere fact that certain measures are recited in mutually different dependent claims does not indicate that a combination of these measures cannot be used to advantage.

What is claimed is:

1. A computer-implemented method of determining efficacy of a substance that is vaporized and inhaled by a user, the method comprising:
    receiving a cartridge within a housing of a vapor inhalation device, the cartridge storing a substance in liquid or solid form therein, the housing having an opening at a first end thereof;
    measuring a characteristic of the substance in the cartridge;
    receiving, in a receptacle of the vapor inhalation device, a quantity of the substance;
    vaporizing at least a portion of the quantity of the substance received in the receptacle to create a vapor, the vapor being in fluid communication with the opening of the housing;
    causing at least a portion of the vapor to flow through the opening at the first end of the housing;
    measuring a characteristic of the at least a portion of the vapor flowing through the opening;
    receiving, from an ancillary device, a self-reported subjective rating of the user of the vapor inhalation device, the self-reported subjective rating of the user being indicative of a level of pleasure experienced by the user;
    receiving physiological data that is indicative of a physiological or affective state of the user of the vapor inhalation device in real-time as the characteristic of the at least a portion of the vapor is being measured, the physiological or affective state describing a physiological functioning, affect, or activity of the user in response to inhalation of the vapor, the physiological data including heart rate of the user and a facial expression of the user;
    transmitting, via the vapor inhalation device, the measured characteristic of the substance in the cartridge, the measured characteristic of the at least a portion of the vapor, or both, to a data repository that is configured to store and receive data generated by a plurality of vapor inhalation devices pertaining to different users;
    analyzing, using machine learning, the received physiological data, the self-reported subjective rating, and the data in the data repository generated by the plurality of vapor inhalation devices to develop descriptive and predictive models; and
    generating an output for placing the user at a desired affective state based at least in part on the developed descriptive and predictive models,
    wherein the output is configured to cause:
        an adjustment to be made in the quantity of the substance received in the receptacle, an adjustment to be made in at least one of a set of characteristics of the substance stored in the cartridge, a generation of an instruction to replace the substance stored in the cartridge, a generation of an instruction informing the user that the desired affective state is reached, a generation of an instruction informing the user that a next event will exceed the desired affective state, or any combination thereof.

2. The method of claim 1, further comprising analyzing data to generate a geospatial representation of consumption.

3. The method of claim 1, wherein the substance is a first substance, and the output further causes generation of an instruction to replace the first substance with a second substance that is of a different chemical composition from the first substance.

4. The method of claim 1, wherein the cartridge is a first cartridge, and the output further causes generation of an instruction to replace the first cartridge with a second cartridge that is different from the first cartridge.

5. The method of claim 1, wherein the output further causes a modification of a dosing schedule.

6. The method of claim 1, wherein the output further causes a modification of a dosing amount.

7. The method of claim 1, wherein the output further causes a modification of a purchasing schedule.

8. The method of claim 1, wherein the output further causes an adjustment to be made in at least one of a set of characteristics of the substance stored in the cartridge.

9. The method of claim 8, wherein the set of characteristics of the substance includes a turbidity of the substance, a pH level of the substance, a color of the substance, a chemical composition of the substance, a viscosity of the substance, a volume of the substance, a weight of the substance, a flavor of the substance, an expected life of a substance, or any combination thereof.

10. The method of claim 1, wherein the output further causes an adjustment to be made in a time duration or time period of usage of the vapor inhalation device.

11. The method of claim 1, wherein the self-reported subjective rating further includes a level of symptomatic relief to the user, a change in affective state of the user, a change in cognitive state of the user, or any combination thereof.

12. The method of claim 1, further comprising receiving an environmental parameter associated with the user, an affective response of the user, biometric data associated with the user, or any combination thereof.

13. The method of claim 1, further comprising measuring one or more performance metrics of the vapor inhalation device.

14. The method of claim 13, wherein the one or more performance metrics include battery performance, vaporizing element performance, air flow, barometric performance, accelerometer performance, or any combination thereof.

15. The method of claim 1, further comprising measuring an environmental parameter.

16. The method of claim 15, wherein the environmental parameter is a decibel level, an amount of light, a temperature, a humidity percentage, a barometric pressure, an elevation, a geographic location, or any combination thereof.

17. The method of claim 1, further comprising generating, using a camera, a microphone, or any combination thereof, the physiological data that is indicative of the physiological or the affective state of the user of the vapor inhalation device.

18. The method of claim 17, wherein the generated physiological data further includes pupil dilation data, voice data, or any combination thereof.

19. The method of claim 1, wherein the physiological data is associated with a galvanic skin response of the user, a blood pressure of the user, an electroconductivity of skin of the user, a blood volume pulse of the user, a glucose level of the user, a blood oxygen concentration of the user, or any combination thereof.

20. The method of claim 1, wherein the physiological data is received from the ancillary device.

21. The method of claim 1, wherein the physiological data is received from the vapor inhalation device.

22. The method of claim 1, wherein the machine learning includes deep learning or clustering.

23. The method of claim 1, further comprising capturing an image using a camera.

24. The method of claim 1, wherein the cartridge is more than one cartridge.

25. The method of claim 1, further comprising:
measuring an external environmental parameter to determine a context including aggregate circumstances that form a setting for an event, the event including the quantity of the substance being received in the receptacle, and the aggregate circumstances including peer information of nearby devices;
wherein the machine learning further takes as input the measured external environmental parameter when analyzing the received physiological data to generate the output.

26. A computer-implemented method of optimizing efficacy of a substance that is vaporized and inhaled by a user, the method comprising:
receiving a measurement of a characteristic of a substance present in a cartridge of a housing of a vapor inhalation device, the substance being vaporized by the vapor inhalation device to create a vapor;
receiving a measurement of a characteristic of the vapor from the vapor inhalation device;
receiving, from an ancillary device, a self-reported subjective rating of the user of the vapor inhalation device, the self-reported subjective rating of the user being indicative of a level of pleasure experienced by the user;
receiving physiological data that is indicative of a physiological or affective state of the user of the vapor inhalation device in real-time as the characteristic of the vapor is being measured, the physiological or affective state representing a physiological functioning, affect, or activity of the user in response to inhalation of the vapor, the physiological data including heart rate of the user and a facial expression of the user;
wherein the receiving the measured characteristic of the substance in the cartridge, the receiving the measured characteristic of the vapor, or both, includes storing the measured characteristic in a data repository that is configured to store and receive data generated from a plurality of vapor inhalation devices pertaining to different users;
analyzing, using machine learning, the received physiological data, the self-reported subjective rating, and the data stored in the data repository to develop descriptive and predictive models;
generate an output for placing the user at a desired affective state based at least in part on the developed descriptive and predictive models; and
communicating the output to the vapor inhalation device to cause:
an adjustment to be made in a quantity of another substance received in the vapor inhalation device, an adjustment to be made in at least one of a set of characteristics of the substance stored in the cartridge, a generation of an instruction to replace the substance stored in the cartridge, a generation of an instruction informing the user that the desired affective state is reached, a generation of an instruction informing the user that a next event will exceed the desired affective state, or any combination thereof.

* * * * *